(12) United States Patent
Katti et al.

(10) Patent No.: US 6,780,397 B2
(45) Date of Patent: *Aug. 24, 2004

(54) BIOMOLECULE CONJUGATION STRATEGY USING NOVEL WATER-SOLUBLE PHOSPHINE-BASED CHELATING AGENTS

(75) Inventors: Kattesh V. Katti, Columbia, MO (US); Hariprasad Gali, Columbia, MO (US); Wynn A. Volkert, Columbia, MO (US)

(73) Assignee: Curators of the University of Missouri, Columbia, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/386,657

(22) Filed: Aug. 31, 1999

(65) Prior Publication Data
US 2004/0042963 A1 Mar. 4, 2004

Related U.S. Application Data
(60) Provisional application No. 60/098,748, filed on Sep. 1, 1998.

(51) Int. Cl.$^7$ .............................. A61K 49/00; C07F 9/02
(52) U.S. Cl. .................... 424/1.77; 424/1.69; 424/1.65; 568/13
(58) Field of Search .............................. 424/1.65, 1.69, 424/1.77, 1.41, 1.57; 514/800; 530/313; 930/130; 568/13

(56) References Cited

U.S. PATENT DOCUMENTS

| | | | |
|---|---|---|---|
| 4,439,196 A | 3/1984 | Higuchi | 604/890 |
| 4,447,224 A | 5/1984 | DeCant, Jr. et al. | 604/67 |
| 4,447,233 A | 5/1984 | Mayfield | 604/152 |
| 4,475,196 A | 10/1984 | La Zor | 371/29 |
| 4,486,194 A | 12/1984 | Ferrara | 604/897 |
| 4,487,603 A | 12/1984 | Harris | 604/152 |
| 4,925,678 A | 5/1990 | Ranney | 424/493 |
| 4,959,217 A | 9/1990 | Sanders et al. | 424/473 |
| 5,167,616 A | 12/1992 | Haak et al. | 604/20 |
| 5,169,383 A | 12/1992 | Gyory et al. | 604/20 |
| 5,225,182 A | 7/1993 | Sharma | 424/9 |
| 5,455,044 A | 10/1995 | Kim et al. | 424/450 |
| 5,558,852 A | 9/1996 | Bigner et al. | 424/1.49 |
| 5,753,206 A * | 5/1998 | McBride et al. | 424/1.69 |
| 5,772,981 A * | 6/1998 | Govindan et al. | 424/1.49 |

FOREIGN PATENT DOCUMENTS

WO 96/30056 * 10/1996 .......... A61K/51/10

OTHER PUBLICATIONS

Berning, D.E., Katti, K.V,; Singh, P.R.; Higginbotham, C.; Reddy, V.S.; Volkert, W.A. *Nucl. Med. Biol.* 1996, 23, 616.

Betz et al., 1994, Basic Neuroschem. Molecular Cell, (Raven Press Ltd, NY) 5th Ed., 681–699.

Bickel, et al., 1993, Pharmacologic effects in vivo in brain by vector–mediated peptide drug delivery: Proc. Natl. Acad. Sci. USA 90(7)2618–2622.

Brem et al., "Polymers as controlled drug delivery devised for the treatment of malignant brain tumors" *Eur. J. Pharm. Biopham* 39:2–7 (1993).

DeRosch, M.A.; Brodack, J.W.; Grummon, G.D.; Marmino, M.E.; Nosco, D.L.; Deutsch, K.F.; Deutsch, E. *J. Nucl. Med.* 1992, 33, 850.

Forster, A.M,; Storey, A.E.; Archer, C.M.; Nagel, K.R.; Booker, F.S.; Edwards, B.; Gill, H.K.; Kelly, J.D.; McPartlin, M. *J. Nucl. Med.* 1992, 33, 850.

Gilbertson, W.R.; Wang, X, Hoge, G.S., Klug, C.A. Schaefer, J. Synthesis of phosphine–rhodium complexes attached to a standard peptide synthesis resin. *Organometallics* 1996, 15, 4678–4680.

Gilbertson, S.R., Chen, G., McLoughlin, M. Versatile building block for the synthesis of phosphine–containing peptides: The sulfide of diphenylphosphinoserine. *J. Am. Chem. Soc.* 1994, 115, 4481–4482.

Karra, S.R.; Schibli, R.; Katti, K.V.; Gali, H,; Higginbotham, C.; Sieckmann, G.; Hoffman, T.J.; Volkert, W.A. *Bioconjugate Chem.* in preparation (1998).

Lister–James., Moyen, B.R., Dean T. Small peptides radiolabeled with $^{99m}$Tc. Q. *J. Nucl. Med.* 1996, 40, 221–233 and references therein.

Liu, S., Edwards, D.S., Barrett, J.A. $^{99m}$Tc labeling of high potent small peptides. *Bioconjugate Chem.* 1997, 8, 621–636 and references therein.

(List continued on next page.)

Primary Examiner—Michael G. Hartley
(74) Attorney, Agent, or Firm—Kohn & Associates, PLLC

(57) ABSTRACT

This invention describes a novel strategy to produce phosphine-functionalized biomolecules (e.g. peptides or proteins) for potential use in the design and development of site-specific radiopharmaceuticals for diagnosis or therapy of specific cancers. Hydrophilic alkyl phosphines, in general, tend to be oxidatively unstable. Therefore, incorporation of such phosphine functionalities on peptide (and other biomolecule) backbones, without oxidizing the $P^{III}$ centers, is difficult. In this context this discovery reports on a new technology by which phosphines, in the form of bifunctional chelating agents, can be directly incorporated on biomolecular backbones using manual synthetic or solid phase peptide synthesis methodologies. The superior ligating abilities of phosphine ligands, with various diagnostically (e.g. TC-99m) or therapeutically (e.g. Re186/188, Rh-105, Au-199) useful radiometals, coupled with the findings that the resulting complexes demonstrate high in vivo stability makes this approach useful in the development of radiolabeled biomolecules for applications in the design of tumor-specific radiopharmaceuticals.

3 Claims, 2 Drawing Sheets

OTHER PUBLICATIONS

Pardridge, et al., 1992, "Blood–brain barrier and new approaches to brain drug delivery" West J. Med. 156(3) 281–286.

Pardridge, 1992, "Recent Developments in peptide delivery to the brain" Pharm. Toxicol. 71(1):3–10.

Smith, C.J.; Katti, K.V.; Volkert, W.A.; Barbour, L. J. *Inorg. Chem.* 1997, 36, 3928.

Smith, C.J.; Reddy, V.S., Karra, S.R.; Katti, K.V., Barbour, L.J. The synthesis and coordination chemistry of the first water–soluble dithio–bisphospanes ligands. *Inorg. Chem.* 1997, 36, 1786–1791.

Smith, C.J.; Katti, K.V., Volkert, W.A.; Ketring, A.R., Barbour, L.J.: The synthesis and characterization of chemically–flexible, water–soluble dithiobisphosphines. A systemic investigation of the effect of chain–length on the coordination chemistry of rhenium. *Inorg. Chem.* 1997, 36, 3928–3935.

Smith, C.J., Li, N., Katti, K.V., Higginbotham, C., Volkert, W.A. In vitro and in vivo characterization of novel water–soluble dithio–bisphosphine $^{99m}$Tc complexes. *J. Nucl. Biol. Med.* 1997, 24, 685–691.

* cited by examiner

BIOMOLECULE CONJUGATION STRATEGY USING NOVEL WATER-SOLUBLE PHOSPHINE-BASED CHELATING AGENTS

CROSS-REFERENCE TO RELATED APPLICATIONS

This patent application claims the benefit of priority of U.S. Provisional Patent Application Serial No. 60/098,748, filed Sep. 1, 1998, which is incorporated herein by reference.

GRANT INFORMATION

Research in this application was supported in part by a grant from the Department of Energy (DEFG0289ER60875). The government has certain rights in the invention.

TECHNICAL FIELD

This invention relates to development of a new strategy to synthesize biomolecules that can be used to form structure-specific metallated biomolecules. The method provides a facile method using —$PH_2$ intermediates to strategically place phosphine groups at specific sites on biomolecules that will facilitate formation of well-defined complexes on the biomolecule with radiometals and transition metals. These new metallated biomolecules hold potential for applications in the chemical and biomedical fields.

BACKGROUND OF THE INVENTION

The transition metal chemistry of phosphines is diverse, resulting in a myriad of coordination compounds. The wealth of available data on the coordination chemistry of rhenium has provided a strong impetus in extending the chemistry to its diagonally related congener technetium-99. In fact, the demonstration that phosphine ligands produce well-defined, in vitro/in vivo stable complexes with technetium-99m (a γ-emitter with 141 keV and $t_{1/2}$=6.2 h) has resulted in the development of two Tc-99m-based radiopharmaceuticals being currently used for myocardial imaging in humans. [DeRosch et al., 1992; Forster et al., 1992]. Because most human cancer cells express certain affinity for biomolecular vectors such as peptides or proteins, it is conceivable that radiolabeled receptor-avid peptides will provide new vehicles for delivering diagnostic or therapeutic radiations in site-directed treatments. Radiolabeling of receptor-avid peptides (or other bimolecular vectors) is best carried out by using bifunctional chelating agents. Radiolabeling with specific radioisotopes is done at the ligating unit of the bifunctional chelating agent, while functionalities such as —COOH or —NCS will incorporate a biomolecular vector within the bifunctional chelating agent to ultimately produce radiolabeled biomolecules. In this context, the utility of phosphines to construct new bifunctional chelating agents is attractive because of the potential applications of these ligands to produce well-defined complexes with radio-isotopes of diagnostic (Tc-99m) and therapeutic (Re-188, Au-199, Rh-105) value.

However, it may be recognized that chemical transformations of traditional phosphine ligands (e.g. $Ph_2PCH_2CH_2PPh_2$, dppe or $Me_2PCH_2CH_2Pme_2$, dmpe) into bifunctional chelating agents is a challenge. Aryl phosphines (e.g. dppe) which are oxidatively stable are unsuitable for use under in vivo conditions because of their high lipophilicty. On the other hand, alkyl phosphines are oxidatively so unstable that backbone modification and their use in aqueous media would produce corresponding phosphine oxides. Therefore, in order to utilize the superior ligating properties of phosphine ligands in the construction of new bifunctional chelating agents, new strategies on the overall design of phosphine frameworks were needed.

The rich chemistry of phosphines with transition metals makes them well suited for constructing chelating frameworks on simple and complex molecular structures that can be used to form well-defined metallated biomolecules. Metallated biomolecules, where the metal is bound (chelated) in a site-specific and structure-specific manner, hold important potential for a variety of chemical and biomedical applications, including chiral catalysis and radiopharmaceuticals [Gilbertson et al., 1996; Liu et al., 1997; Lister-James, et al., 1996]. In this context, the utility of phosphines to construct metal chelating frameworks either appended to or incorporated within biomolecular structures at specific positions is particularly attractive.

However, it must be recognized that the incorporation of phosphine functionalities in biomolecules by current synthetic strategies is challenging and usually involves lengthy procedures and harsh reaction conditions that often damage (e.g., reduction with Raney nickel) the biomolecule [Gilbertson et al., 1994]. For example, Gilbertson, et al. 1994, employed a reaction pathway to append diphenylphosphine groups that used a diphenylphosphorous (V) sulfide intermediate. After the P=S derivatized peptide was made, reduction of the P=S to the phosphorous (III) phosphine was accomplished with Raney Ni [3] producing a mixture of products where the desired diphosphine-peptide product was produced in low yields. The resulting diphenylphosphine-peptide conjugate was subsequently used to selectively form the corresponding Rh(III) conjugate [Gilbertson et al., 1994].

Recent efforts have been successful in synthesis of bidentate and multidentate chelation frameworks that contain di-hydroxymethylenephosphine (HMP) functionalities [i.e., —$P(CH_2OH)_2$] to facilitate formation of new transition metal complexes [Smith and Reddy et al., 1997; Smith and Katti et al, 1997; Smith and Li et al., 1997]. As a result of this work, the first bifunctional chelating agent containing HMP groups was synthesized, characterized, and used as a vehicle to conjugate metals to biomolecules. The synthesis of this bifunctional chelating agent system (i.e., carboxylate derivative of the di-HMP-di-thia ($P_2S_2$) tetradentate ligand framework shown in Formula 1) was difficult and proceeded via a —P(V)=O intermediate (similar to the Gillickson —P(V)=S intermediate) that had to be reduced with $LiAlH_4$ to a —$P(III)H_2$ intermediate in route to formation of the —$P(CH_2OH)_2$ groups. However, the reduction conditions used would irreversibly alter most biomolecules precluding this approach for synthesis of most phosphine bioconjugates.

To overcome these difficulties, the inventors of the subject inventive method and product have realized and developed the use of —$PH_2$ synthons to form —$P(CH_2OH)_2$ based ligands. Initially, a Br—$(Ch_2)_3PH_2$ reactant was synthesized which demonstrated that it was possible to produce the $P_2S_2$-bifunctional chelating agent:

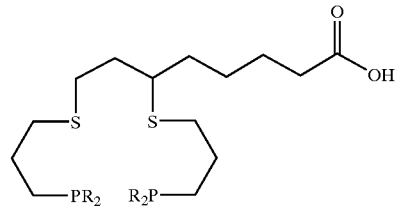

Formula 1

$P_2S_2$—COOH bifunctional chelating agent ($P_2S_2$-BFCA) containing two HMP groups (R=—$CH_2OH$).

This was done without going through the reduction step late in the synthetic scheme (see Schemes 1 and 2). It was unexpected that the utilization of the Br(CH$_2$)$_3$PH$_2$ intermediate in this fashion would be facile given that phosphorous hydrides (e.g., —PH$_2$ containing compounds) are known to have poor oxidative stability. However, these initial syntheses were carried out in organic solvents and care was taken to remove molecular oxygen, except for the rapid conversion of the —PH$_2$ groups to the —P(CH$_2$OH)$_2$ groups by addition of water containing traces of H$_2$CO.

The potential of using HMP-based chelating frameworks for labeling biomolecules with radioactive transition metals (including $^{99m}$Tc and $^{188}$Re) has now been more fully explored. Recent studies of the current inventors demonstrate that $^{99m}$Tc- and Re-complexes with the P$_2$S$_2$—COOH bifunctinal chelating agent (Formula 1) can be covalently linked to peptides to form well defined metal conjugates that have excellent in vitro and in vivo stability. These data provide important evidence that HMP-based metal chelates are useful systems for conjugating biomolecules with transition metals for a variety of chemical and biological applications. The inventors' work with $^{99m}$TC- and Re-P$_2$S$_2$- bioconjugates and other model HMP-based chemical systems demonstrates that HMP-containing ligand frameworks hold important potential for the formulation of new diagnostic and therapeutic radiopharmaceuticals.

SUMMARY OF THE INVENTION

Alkyl substituted phosphines are, in general, oxidatively unstable and, therefore, their backbone chemical modification is difficult especially in the context of appending them on biomolecules (e.g. peptides, proteins and other receptor-avid biomolecules). The current discovery demonstrates that phosphines in the form of functionalized phosphorus(III) hydrides are oxidatively-stable and can be used to achieve chemical modifications. In fact, chemical backbones such as thioethers, amides and amines can be incorporated across —PH$_2$ units without fear of oxidation of the P$^{III}$ center. Further, the carboxylate functionalized (PH$_2$)$_2$S$_2$—COOH bifunctional chelating agent is stable to reaction conditions that are employed during solid phase peptide synthesis (including treatment with HBTU, piperidine, solutions in DMF and washing the resin with trifluoroacetic acid of specific concentrations) for its incorporation on specific biomolecules including peptides (see Schemes 4 and 5). This order of chemical flexibility and oxidative stability of functionalized P$^{III}$ hydrides present realistic prospects in the design and development of radiolabeled biomolecules for use in site-directed diagnosis and therapy of human cancers.

DETAILED DESCRIPTION OF THE INVENTION

Figure 1A:
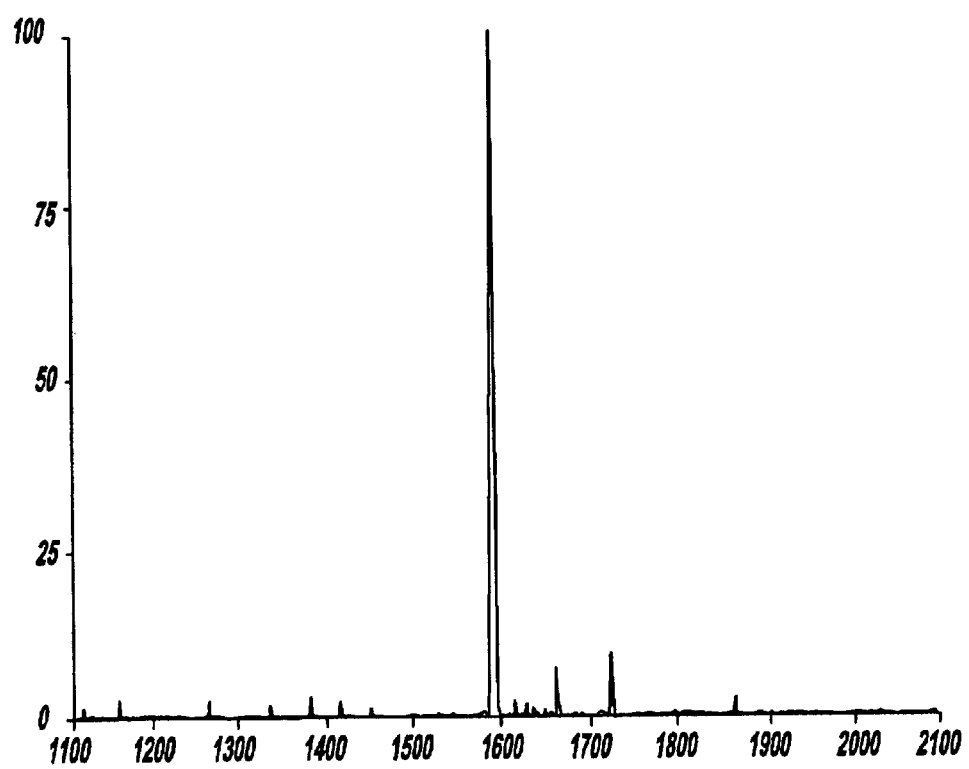
FIG. 1 contains FAB Mass Spectroscopic data and HPLC data for (H$_2$P)$_2$S$_2$-Lys$^6$-[LH-RH].

Detailed investigations from our laboratory have demonstrated that functionalized hydroxymethyl phosphines, such as:

Formula 2

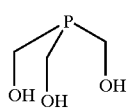

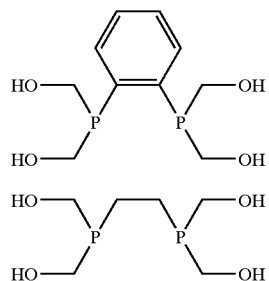

Formula 3

Formula 4 are most suited for use in nuclear medicine because (i) they are soluble in water and display significant oxidative-stability in aqueous media even under high dilutions (1×10$^{-5}$M) and (ii) they produce well-defined and in vivo stable complexes with radiometals of diagnostic (Tc-99m) and therapeutic (Re-188, Au-199, Rh-105) potential [Smith et al., 1997; Berning et al., 1996; Karra et al., 1998]. Therefore, utility of the functionalized hydroxymethyl phosphines and their radiometal complexes for conjugation to biomolecules present realistic opportunities in the design and development of tumor-specific radiopharmaceuticals.

Conjugations of the functionalized hydroxymethyl phosphines or their radiometal complexes to specific biomolecules requires incorporation of a reactive functionality (e.g. —COOH) on their backbone. The synthetic methodology used to produce the functionalized hydroxymethyl phosphines precludes the incorporation of —COOH because it involves a reduction step that uses LiAlH$_4$. However, LiAlH$_4$ would also reduce the —COOH to —CH$_2$OH [Smith et al., 1997].

This inherent synthetic difficulty necessitated the development of a novel synthetic strategy wherein a preformed phosphorus(III) hydride, BrCH$_2$CH$_2$CH$_2$PH$_2$, interacts (and alkylates) within a carboxylate functionalized organic anion (dihydrolipoic acid). The synthesis and characterization of the inventive water-soluble bifunctional chelating agent derived from water-soluble phosphine building units, as taught herein, is shown below in Scheme 1 and Scheme 2.

Scheme 1.
Synthesis of 3-bromopropyl phosphine hydride

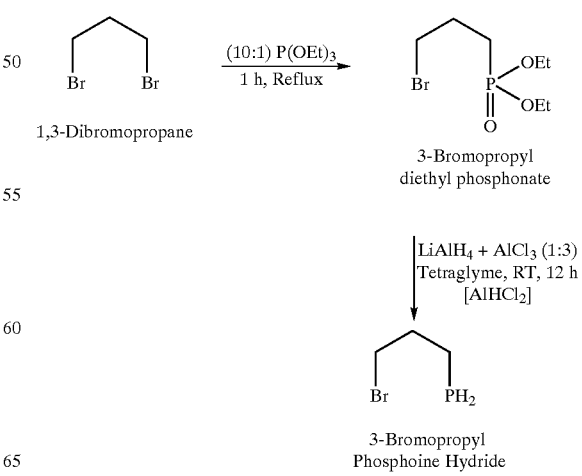

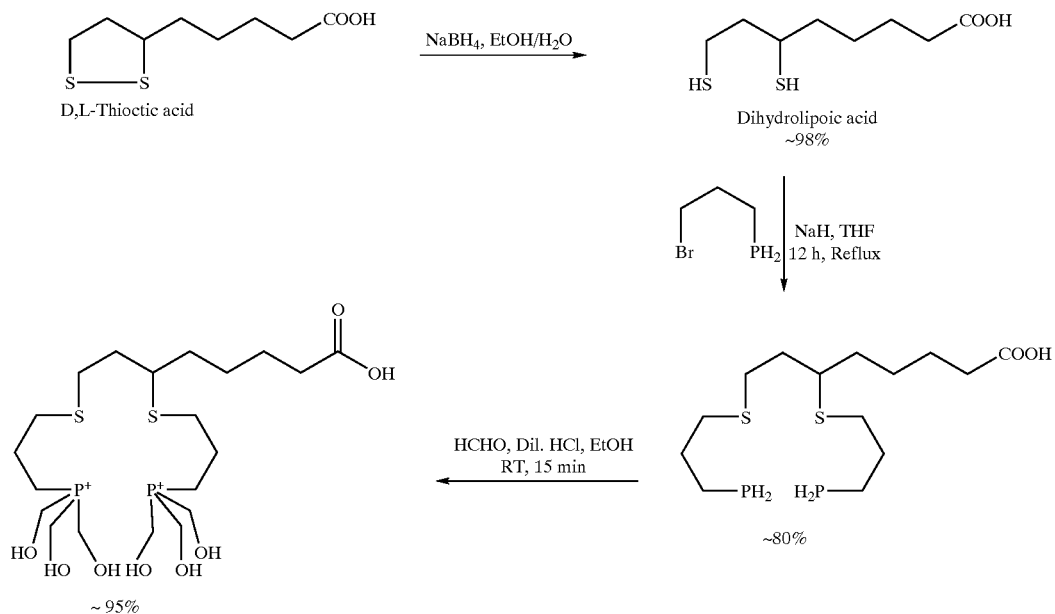
The construction of the corresponding $P_2N_2$—COOH bifunctional chelating agent framework is described in Scheme 3 below:
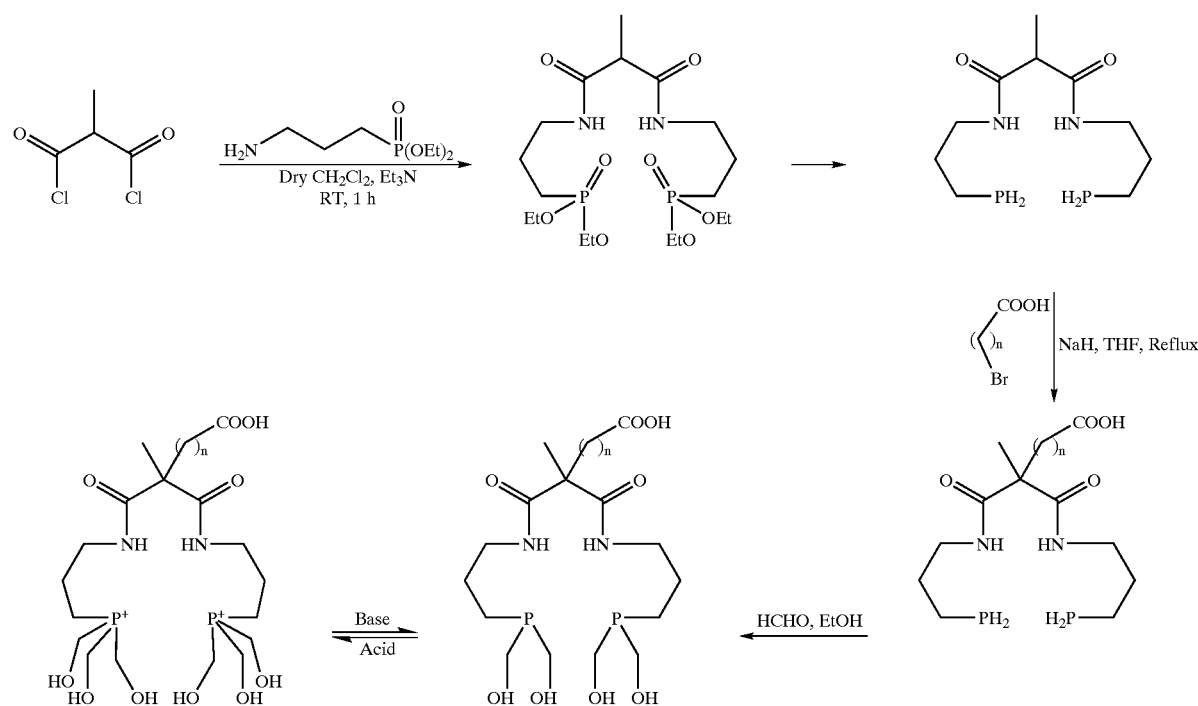

As a result of working with the Br(CH$_2$)$_3$ PH$_2$ intermediate, it was recognized that the intermediate was unexpectedly stable under a variety of storage and reaction conditions. To our surprise, Br(CH$_2$)$_3$ PH$_2$ was reasonably stable in a variety of solvents and over a wide pH range and temperature range. For example, PH$_3$ and the simple methyl- and ethyl-PH$_2$ molecules exhibit poor oxidative stability. However, the —PH$_2$ analogue of the P$_2$S$_2$—COOH, presented below, exhibits different characteristics:

Formula 5

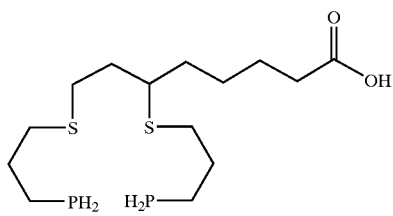

When this analogue was studied under an even wider range of chemical conditions than that used with the Br(CH$_2$)$_3$ PH$_2$ intermediate, (see Experimental), the analogue exhibited a much improved stability profile. Furthermore, the reactivity of the —PH$_2$ groups in these compounds toward molecules containing a wide spectrum of functional groups (including carboxylic acids, amines, thiols, and proteins) was remarkably low or non-measurable. To the inventors' knowledge, this constitutes the first disclosure of compounds containing —PH$_2$ groups that exhibit the degree of stability and non-reactivity which is set forth in this application.

Results of these studies suggested the possibility that appropriate —PH$_2$ containing compounds would be useful for synthesis of —PH$_2$ containing biomolecules, either via linking —PH$_2$ groups to or incorporation of —PH$_2$ groups in the biomolecular structure.

In order to determine the feasibility of linking —PH$_2$ group-containing compounds to biomolecules, the —COOH group on the (PH$_2$)$_2$—S$_2$—COOH bifunctional chelating agent shown in Formula 5 above was activated (i.e., HBTU activator) and subsequently reacted with the free primary amine group on peptides to form an amine linkage. In one case, the activated bifunctional chelating agent reacted with the N-terminal amine group on diglycine. After synthesis and purification, the —PH$_2$ diglycine conjugate was shown to be formed in high yields with the —PH$_2$ groups remaining intact.

Scheme 4.
Coupling of GlyGlyEster tO (PH$_2$)$_2$S$_2$COOH

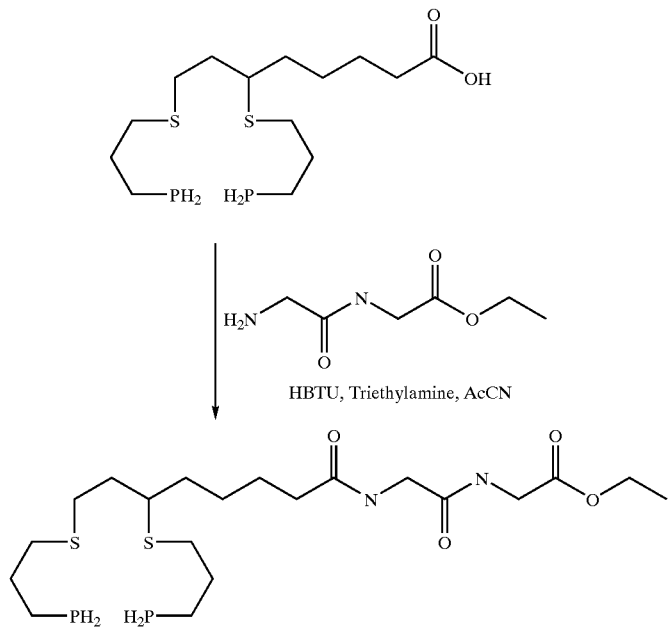

A more stringent reaction sequence was performed to study the ability of the —PH$_2$ groups on the (PH$_2$)$_2$S$_2$—COOH-bifunctional chelating agent to survive a complex reaction sequence. For these studies, a (PH$_2$)$_2$-S-D-Lys conjugate was prepared and then used to synthesize a (PH$_2$)$_2$-S$_2$-conjugate of a peptide (i.e., a D-Lys[6]-LH-RH conjugate) by automated solid phase peptide synthesis (SPPS).

Scheme 5.

Incorportion of (PH$_2$)$_2$S$_2$—COOH on D-Lys$^6$-LH-RH peptide using SPPS

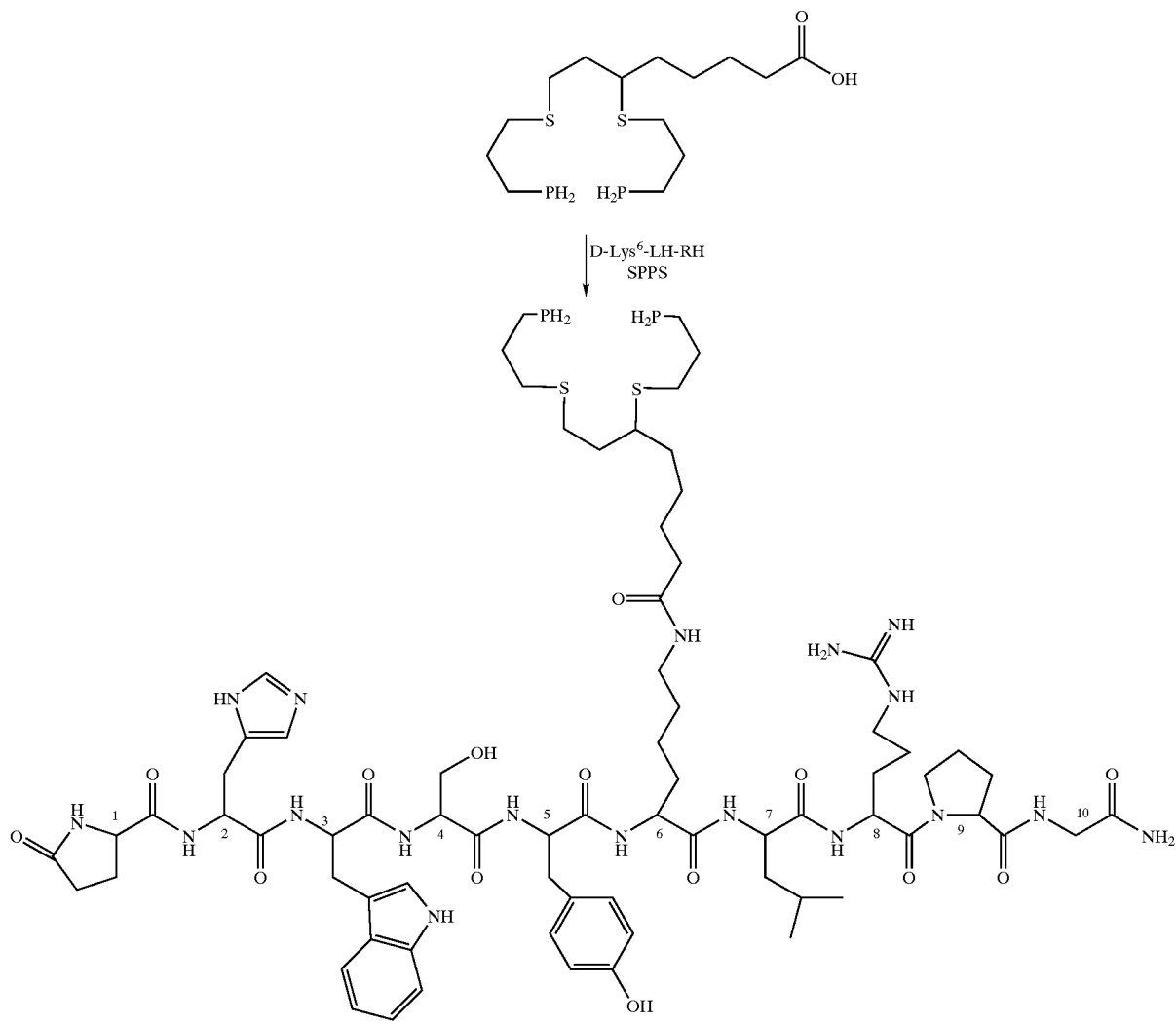

Figure 1B:
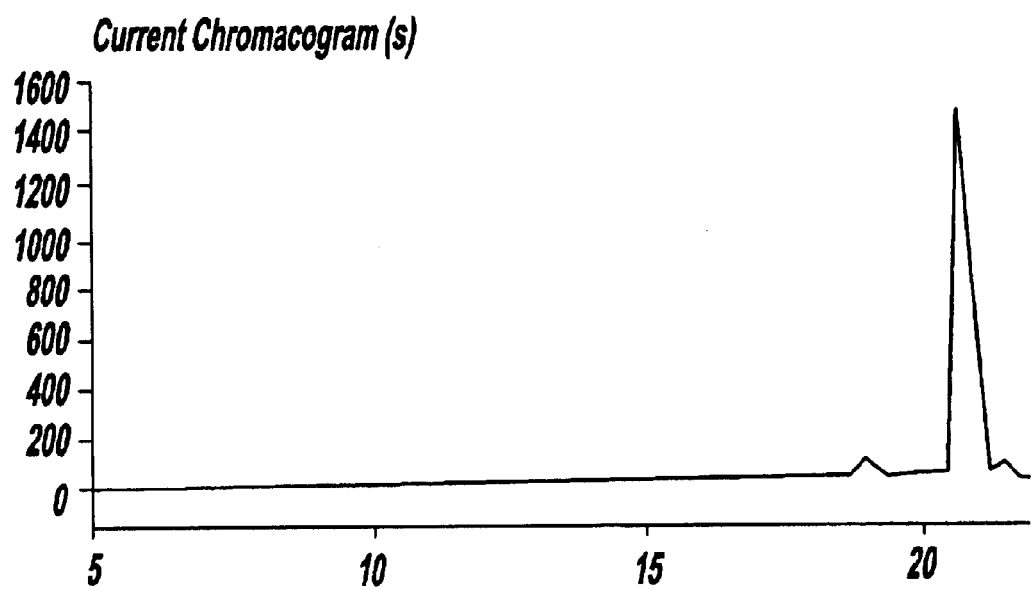
Figure 1C:
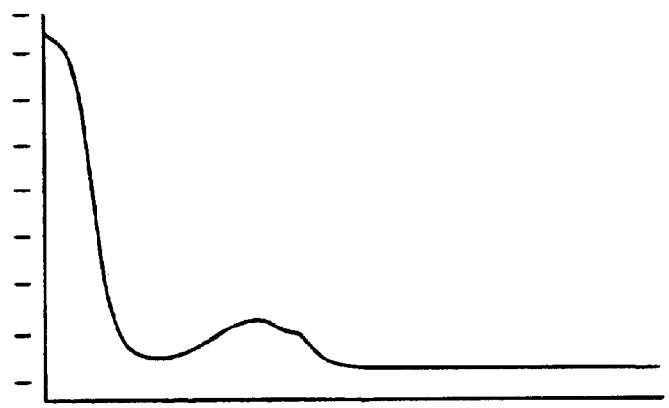

Utilization of the automated SPPS method involved repetitive steps that utilize a variety of chemicals in high concentrations, including TFA for cleavage of the peptide from the resin. The resultant peptide was purified by HPLC and analyzed (by $^1$H and $^{31}$P NMR and High Resolution FAB Mass Spec), demonstrating that the expected product was formed in high yields with no modification of the —PH$_2$ groups (see FIG. 1).

These results demonstrate that the —PH$_2$ groups on this bifunctional chelating agent are resistant to oxidation and have no reactivity with any functional groups on the LH-RH peptide or with the chemicals used during SPPS and analysis. These data also provide evidence that —PH$_2$ groups appended to likely chemical backbones can be used as synthetic intermediates to synthesize —PH$_2$ group-conjugated biomolecules.

The reasons for the unexpectedly high oxidative stability of —PH$_2$ groups and low chemical reactivity are not fully understood. However, appending the —PH$_2$ groups, via a hydrocarbon backbone, to larger molecular backbones can produce major deactivation of the oxidative and chemical reactivity of these groups. After synthesis of —PH$_2$ derivatized biomolecules, it is possible to convert the —PH$_2$ groups to other phosphines including, for example, HMP groups. Aldehyde groups are one class of functionalities that will react rapidly with —PH$_2$ groups. Thus, the —PH$_2$ groups can be converted, in a rapid and facile manner (e.g., in aqueous solutions over a wide -pH range), by reaction with aldehydes to produce the corresponding —PR$_2$ groups.

For example, formaldehyde rapidly reacts with —PH$_2$ groups to form —P(CH$_2$OH)$_2$ groups. Either the —PH$_2$ groups or the —PR$_2$ groups (converted from —PH$_2$ groups) can be used as part of a chelator framework on the biomolecule, to form well defined, stable complexes with transition metals to produce the metallated conjugate.

It is possible to synthesize biomolecules, for example, steroids, peptides and proteins, with chiral centers at specific points in their backbone. Incorporation of ligating centers capable of coordination with catalytically useful transition metals, for example, Rh(I), Pd(II), and Re(I–V) at specific positions of chiral biomolecules will lead to the design and development of enautioselective transition metal catalysts.

Incorporation of alkyl or aryl phosphine ligands on biomolecules is difficult because under the reaction conditions that are generally employed, for example, dimethyl formamide solvent, or trifluoroacetic treatment, phosphines are oxidized to their corresponding phosphine oxides. In this context, the utility of phosphines, in the form of $PH_2$ precursors, as described in Schemes 1 and 2 above is unique.

This invention also provides avenues for the incorporation of chiral centers on phosphine backbones. The resulting transition metal complexes of chiral center functionalized phosphines are important due to applications as enautioselective catalysts in the synthesis of fine chemicals and pharmaceutical intermediates.

Thus, according to the present invention, $—PH_2$ containing reagents (synthons) provide an important new approach for syntheses of $—PH_2$ containing biomolecules by virtue of their unexpectedly high oxidative stability and low chemical reactivity. The $—PH_2$ groups can be readily converted to other $—PR_2$ functionalities, for example, $R=—CH_2OH$. Without the use of this new synthetic approach it is extremely difficult, if not impossible, to synthesize $—PR_2$ containing biomolecules. These phosphine groups appended to biomolecules at selected molecular sites can be used to complex transition metal conjugates. Examples of $^{9m}Tc$ complexation reactions with biomolecule conjugated $(P_2H_2)_2S_2$ ligands are outlined in Scheme 6. These metallated biomolecules can be used in a variety of chemical, including, for example, chiral catalys, and biomedical, including, for example, radiopharmaceutical applications [Gilbertson et al., 1996; Liu et al., 1997; Lister-James, et al., 1997; Gilbertson, et al., 1994].

Scheme 6.
$^{99m}Tc$ complexation of peptide coupled $(PH_2)_2S_2—COOH$
(Examples of pre-conjugation strategy)

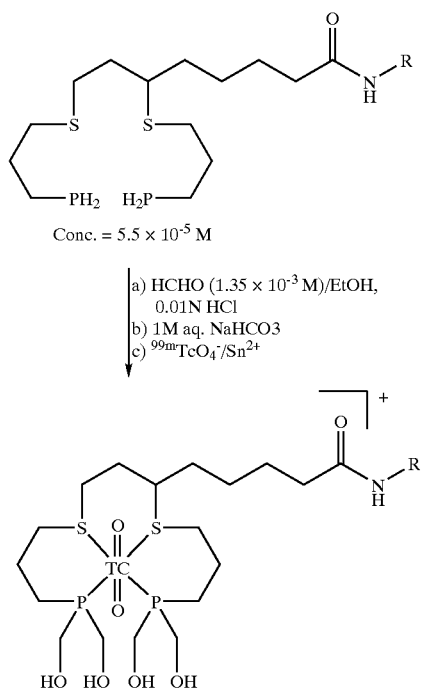

R = GlyGlyOEt or Lys$^6$-LH-RH $^{99m}$Tc-complex yield ~90%
$^{99m}$Tc-complex stable in pH range 5–8 for > 24 h Experimental Details on $(P_2H_2)_2S_2$—COOH ligand synthesis, incorporations on GlyGly and D-Lys$^6$(LH-RH) peptides and complexation reactions with $^{99m}Tc$ are summarized hereinbelow.

Synthesis of 3-bromo-propyl phosphine hydride (Scheme 1)

Powdered $LiAlH_4$ 5 g (135 mmol) was taken in tetraglyme 300 ml and the suspension was cooled to 0° C. in an ice bath. Then anhydrous $AlCl_3$ powder 55 g (412 mmol) was added slowly in small portions and the suspension was stirred for thirty minutes. Diethyl-3-bromopropyl phosphonate 23 g (89 mmol) was added dropwise and the reaction mixture was stirred for 12 hours at room temperature. Finally, 3-bromopropyl phosphine hydride was obtained by vacuum distillation of reaction mixture at 110° C. under pressure of 2.5 mm and was collected directly in the trap maintained at −77° C. Product thus obtained contains a small amount (~10%) of solvent tetraglyme and was used without any further purification. Yield of the product was 12 g (77%). Extreme care was taken in handling of phosphine. $^1H$ NMR (CDCl$_3$): 1.99 (bm, BrCH$_2$C$\underline{H}_2$CH$_2$PH$_2$, 2H), 2.32 (bm, BrCH$_2$CH$_2$C$\underline{H}_2$PH$_2$, 2H), 2.98 (bm, BrCH$_2$CH$_2$CH$_2$P$\underline{H}_2$, 2H), 3.32 (m, BrC$\underline{H}_2$CH$_2$CH$_2$PH$_2$, 2H) $^{13}C$ NMR (CDCl$_3$): 12.59 (d, J$_{P-C}$=9.2 Hz, BrCH$_2$CH$_2$$\underline{C}$H$_2$PH$_2$), 33.72 (s, BrCH$_2$$\underline{C}$H$_2$CH$_2$PH$_2$), 35.81 (s, Br$\underline{C}$H$_2$CH$_2$CH$_2$PH$_2$) $^{31}P$ NMR (CDCl$_3$): −138.37 (s, BrCH$_2$CH$_2$CH$_2$P$\underline{H}_2$)

Synthesis of H$_2$P(CH$_2$)$_3$SCH$_2$CH$_2$CH((CH$_2$)$_4$COOH)S(CH$_2$)$_3$PH$_2$ (Scheme 2)

A sample of 60% NaH in mineral oil 6.2 g (155 mmol) was washed with 25 ml of dry hexane and then suspended in 200 ml of freshly distilled dry tetrahydrofuran and the suspension was cooled to 0° C. in an ice bath. Then a solution of DL-6,8-dihydro-thioctic acid 8.5 g (41 mmol) in 25 ml dry tetrahydrofuran was added dropwise slowly to the suspension. After stirring the reaction mixture for 15 minutes at 0° C., a solution 3-bromopropyl phosphine hydride 12 g (77.4 mmol) in 25 mi dry tetrahydrofuran was added dropwise slowly. The ice bath was replaced by oil bath and the reaction mixture was refluxed for 12 hours under nitrogen. The excess NaH was quenched using a minimum amount of saturated sodium sulfate solution and the solution was filtered through a pad of silica gel. The solvent was removed on a rotavap and chromatographed in a silica gel column using hexane/ethyl acetate solvent system for elution to obtain a pure bisphosphine hydride 10.8 g (78%) as a colorless viscous oil. Low-resolution HRF AB-Ms: Calculated for $C_{14}H_{30}O_2P_2S_2$ 356.1162, found [M+H]$^+$, m/z 357.1237. $^1H$ (CDCl$_3$): 1.44–1.61 (m, SCH$_2$CH$_2$C$\underline{H}_2$$^a$PH$_2$, SCH$_2$CH$_2$C$\underline{H}_2$$^b$PH$_2$, CHCH$_2$C$\underline{H}_2$CH$_2$CH$_2$COOH), 1.69–1.78 (m, SCH$_2$C$\underline{H}_2$CH$_2$$^a$PH$_2$, SCH$_2$C$\underline{H}_2$CH$_2$$^b$PH$_2$, CHCH$_2$CH$_2$C$\underline{H}_2$CH$_2$COOH), 2.29–2.34 (m, CHCH$_2$CH$_2$CH$_2$C$\underline{H}_2$COOH, 2.46–2.66 (m, C$\underline{H}_2$CH$_2$CH$_2$$^a$PH$_2$, C$\underline{H}_2$CH$_2$CH$_2$$^b$PH$_2$, SC$\underline{H}_2$C$\underline{H}_2$CH(C$\underline{H}_2$)S), 2.93–2.99 (m, CH$_2$CH$_2$CH$_2$$^a$P$\underline{H}_2$, CH$_2$CH$_2$CH$_2$$^b$P$\underline{H}_2$), 11.45 (bs, CHCH$_2$CH$_2$CH$_2$CH$_2$COO$\underline{H}$) $^{13}C$ (CDCl$_3$): 13.46 (t, J$_{P-C}$= 13.8 Hz, CH$_2$CH$_2$$\underline{C}$H$_2$$^a$PH$_2$, CH$_2$CH$_2$$\underline{C}$H$_2$$^b$PH$_2$), 24.9 (s, CHCH$_2$$\underline{C}$H$_2$CH$_2$CH$_2$COOH),26.62 (s, CHCH$_2$CH$_2$$\underline{C}$H$_2$CH$_2$COOH), 29.72 (s, CH$_2$$\underline{C}$H$_2$SCH$_2$CH$_2$CH$_2$$^b$PH$_2$), 31.23 (d, $^2$J$_{P-C}$=8.8 Hz, SCH$_2$$\underline{C}$H$_2$CH$_2$$^b$PH$_2$), 33.05 (m, S$\underline{C}$H$_2$CH$_2$CH$_2$$^b$PH$_2$SCH$_2$$\underline{C}$H$_2$CH$_2$$^a$PH$_2$), 33.38 (d, $^3$J$_{P-C}$, S$\underline{C}$H$_2$CH$_2$CH$_2$$^a$PH$_2$), 34.34 (s, CH$\underline{C}$H$_2$CH$_2$CH$_2$CH$_2$COOH), 35.02 (s, $\underline{C}$H$_2$CH$_2$SCH$_2$CH$_2$CH$_2$$^b$PH$_2$), 35.08 (s, CHCH$_2$CH$_2$CH$_2$CH$_2$$\underline{C}$OOH) $^{31}P$ (CDCl$_3$): −136.38

(s,$^b$PH$_2$), −136.34 (s, $^a$PH$_2$) $^{31}$P (Proton coupled, CDCl$_3$): −136.29 (t, J$_{P-H}$=193.2 Hz, J$^1_{P-H}$=4.9 Hz, $^b$PH$_2$), −136.24 (t, J$_{P-H}$=193.2 Hz, J$^1_{P-H}$=4.9 Hz, $^a$PH$_2$)

Synthesis of H$_2$P(CH$_2$)$_3$SCH$_2$CH$_2$CH((CH$_2$)$_4$CONHGlyGlyOEt)S(CH$_2$)$_3$PH$_2$ (Scheme 4)

To a solution of (PH$_2$)$_2$S$_2$—COOH (500 mg, 1.4 mmol), GlyGlyOEt.HCl (277 mg, 1.41 mmol) and triethylamine (700 mg, 6.93 mmol) in acetonitrile (20 ml) was added O-Benzotriazolyl-N,N,N',N'-tetramethyluronium Hexafluorophosphate (HBTU) (538 mg, 1.42 mmol). After the reaction mixture was stirred at room temperature for 15 minutes, the solvent was removed and the crude product was chromatographed on a silica gel. Pure product was obtained by eluting with 3:2 hexanes and ethyl acetate solvent mixture. Yield is 350 mg (65%). HRFAB-MS: Calculated for C$_{20}$H$_{40}$O$_4$N$_2$P$_2$S$_2$ 498.1905, found [M+H]$^+$, m/z 499.1998 $^1$H (CDCl$_3$): 1.16–1.28 (t, 3H), 1.35–1.64(m, 9H), 1.65–1.88 (m, 7H), 2.18–2.24 (t, 2H), 2.28–2.35 (m, 2H), 2.43–2.79 (m, 8H)), 2.95–3.02 (m, 2H), 3.91–4.07 (m, 3H), 4.11–4.29 (q, 2H), 6.32–6.43 (t, 1H), 6.67–6.89 (t, 1H) $^{13}$C (CDCl$_3$): 13.49 (dd), 14.55(s), 2882(s), 26.87(s), 29.79(s), 31.31(s), 33.17(s), 33.40(s), 35.17(d), 41.75(s), 43.75(s), 45.13(s), 62.09(s), 169.66(s), 169.98(s), 174.02(s) $^{31}$P (CDCl$_3$): −136.50(s), −136.56(s).

H$_2$P(CH$_2$)$_3$SCH$_2$CH$_2$CH((CH$_2$)$_4$CONH-Lys$^6$-LHRH)S(CH$_2$)$_3$PH$_2$ was synthesized by using solid phase peptide synthesis (Scheme 5).

Complexation with $^{99m}$Tc (Scheme 6)

The pre conjugated (PH$_2$)$_2$S$_2$-GlyGlyOEt and (PH$_2$)$_2$S$_2$-Lyx$^6$[LH-RH] produced $^{99m}$Tc complexes in >95% upon treatment with $^{99m}$TcO$_4^-$ in the presence of Sn$^{+2}$. In all these complexations, formylation of —PH$_2$ units to —P(CH$_2$OH)$_2$ occurred in situ upon treatment with 37% aqueous formaldehyde. Complexation details are summarized in Scheme 6.

Delivery of Products/Therapeutics

The phosphine-functionalized biomolecules may be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein may be thus determined by such considerations as are known in the art. The amount must be effective to achieve improvement including but not limited to diagnosis and therapy and to improved survival rate or more rapid recovery, or improvement or elimination of symptoms and other indicators as are selected as appropriate measures by those skilled in the art.

In the method of the present invention, the phosphine-functionalized biomolecules can be administered in various ways. It should be noted that the phosphine-functionalized biomolecules can be administered as the compound or as the pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular. Intraperitoneally, and intranasal administration, as well as intrathecal and infusion techniques. Implants of the compounds are also useful. The patient being treated is a warm-blooded animal and, in particular, mammals including man. The pharmaceutically acceptable carriers, diluents, adjuvants, and vehicles as well as implant carriers generally refer to inert, non-toxic solid or liquid fillers, diluents or encapsulating material which are not reactive with the active ingredients of the invention.

The doses may be single doses or multiple doses over a period of several days to several months or until diminution of the disease is achieved. The treatment generally has a length proportional to the length of the disease process and drug effectiveness and the patient species being treated. Optimal dosing schedules may be calculated using measurements of drug accumulation in the body. Practitioners of ordinary skill in the art can readily determine optimum dosages, dosing methodologies, and repetition rates. Optimum dosages may vary depending on the relative potency of phosphine-functionalized biomolecules, and can generally be determined based on ED$_{50}$ values in in vitro and in vivo animal studies and clinical trials.

When administering the phosphine-functionalized biomolecules parenterally, the phosphine-functionalized biomolecules will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such as cotton seed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the phosphine-functionalized biomolecules can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems and modules are well known to those skilled in the art.

A pharmacological formulation of the phosphine-functionalized biomolecules utilized in the present invention can be administered orally to the patient. Conventional methods such as administering the compounds in tablets, suspensions, solutions, emulsions, capsules, powders, syrups and the like are usable.

Known techniques which deliver the phosphine-functionalized biomolecules orally, subcutaneously or parenterally including intravenous, intraarterial, intramuscular, intraperitoneally, and intranasal administration as well as intrathecal and infusion techniques and retain the biological activity are preferred.

For delivery within the CNS intrathecal delilvery can be used with, for example, an Ommaya reservoir. U.S. Pat. No. 5,455,044 provides for use of a dispersion system for CNS delivery or see U.S. Pat. No. 5,558,852 for a discussion of CAN delivery. In addition, pharmacological formulations that cross the blood-brain barrier can be administered. [Betz et al., 1994; Brem et al., 1993]. Such formulations can take advantage of methods now available to produce chimeric peptides in which the present invention is coupled to a brain transport vector allowing transportation across the barrier [Pardridge, et al., 1992; Pardridge, 1992; Bickel, et al., 1993]. Further, in appropriate cases, blood-brain barrier disruption can be utilized [Neuwelt et al., 1980].

In one embodiment, the phosphine-functionalized biomolecules can be administered initially by intravenous injection to bring blood levels of phosphine-functionalized biomolecules to a suitable level. The patient's phosphine-functionalized biomolecule levels are then maintained by an oral dosage form, although other forms of administration, dependent upon the patient's condition as indicated above, can be used. The quantity of phosphine-functionalized biomolecules to be administered will vary for the patient being treated and will vary from about 100 ng/kg of body weight to 100 mg/kg of body weight per day and preferably will be from 10 μg/kg to 10 mg/kg per day.

Reference

Berning, D. E.; Katti, K. V.; Singh, P. R.; Higginbotham, C.; Reddy, V. S.; Volkert, W. A. Nucl. Med. Biol. 1996, 23, 616.

Betz et al., 1994, Basic Neurochem. Molecular Cell, (Raven Press Ltd, NY) 5th Ed., 681–699.

Bickel, et al., 1993, "Pharmacologic effects in vivo in brain by vector-mediated peptide drug delivery" Proc. Natl. Acad. Sci. USA 90(7)2618–2622

Brem et al., "Polymers as controlled drug delivery devised for the treatment of malignant brain tumors" Eur. J. Pharm. Biopharm 39:2–7 (1993)

DeRosch, M. A.; Brodack, J. W.; Grummon, G. D.; Marmino, M. E.; Nosco, D. L.; Deutsch, K. F.; Deutsch, E. J. Nucl. Med. 1992, 33, 850.

Forster, A. M.; Storey, A. E.; Archer, C. M.; Nagel, K. R.; Booker, F. S.; Edwards, B.; Gill, H. K.; Kelly, J. D.; McPartlin, M. J. Nucl. Med. 1992, 33, 850.

Gilbertson, W. R., Wang, X, Hoge, G. S., Klug, C. A. Schaefer, J. Synthesis of phosphine-rhodium complexes attached to a standard peptide synthesis resin. Organometallics 1996, 15, 4678–4680.

(a) Liu, S., Edwards, D. S., Barrett, J. A. $^{99m}$Tc labeling of high potent small peptides. Bioconjugate Chem. 1997, 8, 621–636 and references therein.

(b) Lister-James, J., Moyen, B. R., Dean T. Small peptides radiolabeled with $^{99m}$Tc. Q. J. Nucl. Med. 1996, 40, 221–233 and references therein.

Gilbertson, S. R., Chen, G., McLoughlin, M. Versatile building block for the synthesis of phosphine-containing peptides: The sulfide of diphenylphosphinoserine. J. Am. Chem. Soc. 1994, 116, 4481–4482

Karra, S. R.; Schibli, R.; Katti, K. V.; Gali, H.; Higginbotham, C.; Sieckmann, G.; Hoffman, T. J.; Volkert, W. A. Bioconjugate Chem. in preparation (1998).

Pardridge, et al., 1992, "Blood-brain barrier and new approaches to brain drug delivery" West J. Med. 156(3) 281–286

Pardridge, 1992, "Recent Developments in peptide drug delivery to the brain" Pharm. Toxicol. 71(1):3–10

Smith, C. J.; Li, N.; Katti, K. V.; Higginbotham, C.; Volkert, W. A. J. Nucl. Biol. Med. 1997, 24, 658.

Smith, C. J.; Katti, K. V.; Volkert, W. A.; Barbour, L. J. Inorg. Chem. 1997, 36, 3928.

Smith, C. J., Reddy, V. S., Karra, S. R., Katti, K. V., Barbour, L. J. The synthesis and coordination chemistry of the first water-soluble dithio-bisphosphanes ligands. Inorg. Chem. 1997, 36, 1786–1791.

Smith, C. J., Katti, K. V., Volkert, W. A., Ketring, A. R., Barbour, L. J.: The synthesis and characterization of chemically-flexible, water-soluble dithio-bisphosphines. A systematic investigation of the effect of chain-length on the coordination chemistry of rhenium. Inorg. Chem. 1997, 36, 3928–3935.

Smith, C. J.; Li, N., Katti, K. V., Higginbotham, C., Volkert, W. A. In vitro and in vivo characterization of novel water-soluble dithio-bisphosphine $^{99m}$Tc complexes. J. Nucl. Biol. Med. 1997, 24, 685–691.

What we claim is:

1. A conjugated biomolecule comprising:
a biomolecule; and
an intermediate having the formula:

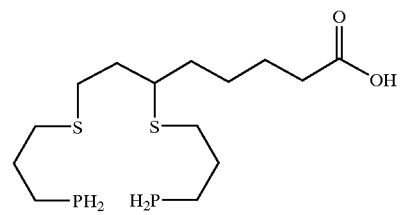

conjugated to said biomolecule.

2. An intermediate for forming a radiopharmaceutical, said intermediate having the formula

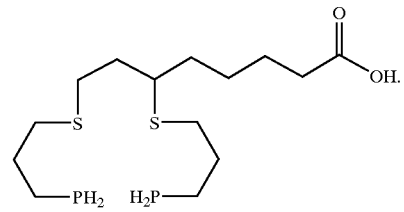

3. A conjugate for forming a radiopharmaceutical comprising the intermediate according to claim 2, which is coupled to the N-terminus of a peptide.

* * * * *